US006702983B2

(12) United States Patent
Hu et al.

(10) Patent No.: US 6,702,983 B2
(45) Date of Patent: Mar. 9, 2004

(54) LOW IONIC STRENGTH METHOD AND COMPOSITION FOR REDUCING BACTERIAL ATTACHMENT TO BIOMATERIALS

(75) Inventors: Zhenze Hu, Pittsford, NY (US); Joseph C. Salamone, Boca Raton, FL (US); Roya Borazjani, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 491 days.

(21) Appl. No.: 09/855,575

(22) Filed: May 15, 2001

(65) Prior Publication Data

US 2003/0031587 A1 Feb. 13, 2003

(51) Int. Cl.$^7$ .................................................. A61L 2/00

(52) U.S. Cl. ............................... 422/1; 422/28; 422/40; 526/245; 526/279

(58) Field of Search ............................... 422/1, 40, 28; 526/245, 279

(56) References Cited

U.S. PATENT DOCUMENTS

| 4,055,378 | A | 10/1977 | Feneberg et al. ............ 351/160 |
|---|---|---|---|
| 4,096,315 | A | 6/1978 | Kubacki ...................... 428/412 |
| 4,122,942 | A | 10/1978 | Wolfson ...................... 206/5.1 |
| 4,136,250 | A | 1/1979 | Mueller et al. ............... 528/29 |
| 4,143,949 | A | 3/1979 | Chen ........................... 351/160 |
| 4,153,641 | A | 5/1979 | Deichert et al. ............ 260/827 |
| 4,214,014 | A | 7/1980 | Hofer et al. .................. 427/40 |
| 4,217,038 | A | 8/1980 | Letter et al. ............. 351/160 R |
| 4,312,575 | A | 1/1982 | Peyman et al. ......... 351/160 H |
| 4,321,261 | A | 3/1982 | Ellis et al. ................... 424/180 |
| 4,436,730 | A | 3/1984 | Ellis et al. ................... 424/180 |
| 4,463,149 | A | 7/1984 | Ellis ............................ 526/279 |
| 4,565,083 | A | 1/1986 | Thompson ....................... 72/98 |
| 4,604,479 | A | 8/1986 | Ellis ............................ 556/440 |
| 4,631,435 | A | 12/1986 | McCarty ...................... 310/156 |
| 4,632,844 | A | 12/1986 | Yanagihara et al. .......... 427/38 |
| 4,686,267 | A | 8/1987 | Ellis et al. ................... 526/245 |
| 4,740,533 | A | 4/1988 | Su et al. ...................... 523/106 |
| 4,826,936 | A | 5/1989 | Ellis ............................ 526/258 |
| 4,910,277 | A | 3/1990 | Bambury et al. ............ 526/260 |
| 4,996,275 | A | 2/1991 | Ellis et al. ................... 526/245 |
| 5,006,622 | A | 4/1991 | Kunzler et al. .............. 526/309 |
| 5,032,658 | A | 7/1991 | Baron et al. ................. 526/321 |
| 5,034,461 | A | 7/1991 | Lai et al. ..................... 525/100 |
| 5,070,215 | A | 12/1991 | Bambury et al. ............ 556/418 |
| 5,091,204 | A | 2/1992 | Ratner et al. .................. 427/2 |
| 5,153,072 | A | 10/1992 | Ratner et al. ............... 428/461 |
| 5,177,165 | A | 1/1993 | Valint, Jr. et al. ........... 526/245 |
| 5,177,168 | A | 1/1993 | Baron et al. ................. 526/321 |
| 5,219,965 | A | 6/1993 | Valint, Jr. et al. ........... 526/245 |
| 5,236,969 | A | 8/1993 | Kunzler et al. .............. 523/108 |
| 5,260,000 | A | 11/1993 | Nandu et al. ................ 264/2.1 |
| 5,270,418 | A | 12/1993 | Kunzler et al. .............. 526/309 |
| 5,298,533 | A | 3/1994 | Nandu et al. ................ 523/106 |
| 5,310,779 | A | 5/1994 | Lai ............................. 524/588 |
| 5,321,108 | A | 6/1994 | Kunzler et al. .............. 526/242 |
| 5,336,797 | A | 8/1994 | McGee et al. ............... 556/419 |
| 5,346,976 | A | 9/1994 | Ellis et al. ................... 526/279 |
| 5,358,995 | A | 10/1994 | Lai et al. ..................... 525/547 |
| 5,364,918 | A | 11/1994 | Valint, Jr. et al. ........... 526/245 |
| 5,387,662 | A | 2/1995 | Kunzler et al. .............. 526/245 |
| 5,401,327 | A | 3/1995 | Ellis et al. ..................... 134/42 |
| 5,405,878 | A | 4/1995 | Ellis et al. ..................... 422/28 |
| 5,449,729 | A | 9/1995 | Lai ............................. 526/286 |
| 5,500,144 | A | 3/1996 | Potini et al. ............. 252/174.15 |
| 5,512,205 | A | 4/1996 | Lai ......................... 252/182.14 |
| 5,539,016 | A | 7/1996 | Kunzler et al. .............. 523/107 |
| 5,604,189 | A | 2/1997 | Zhang et al. ................ 510/112 |
| 5,610,204 | A | 3/1997 | Lai ............................... 522/44 |
| 5,610,252 | A | 3/1997 | Bambury et al. ............ 526/279 |
| 5,616,757 | A | 4/1997 | Bambury et al. ............ 556/419 |
| 5,639,908 | A | 6/1997 | Lai ............................. 560/158 |
| 5,645,827 | A | 7/1997 | Marlin et al. ............. 424/78.04 |
| 5,648,515 | A | 7/1997 | Lai ............................. 560/115 |
| 5,708,094 | A | 1/1998 | Lai et al. ..................... 525/296 |
| 5,710,302 | A | 1/1998 | Kunzler et al. .............. 556/434 |
| 5,711,823 | A | 1/1998 | Ellis et al. ..................... 134/42 |
| 5,714,557 | A | 2/1998 | Kunzler et al. .............. 526/279 |
| 5,726,733 | A | 3/1998 | Lai et al. ..................... 351/160 |
| 5,773,396 | A | 6/1998 | Zhang et al. ................ 510/115 |
| 5,824,719 | A | 10/1998 | Kunzler et al. .............. 523/106 |

(List continued on next page.)

FOREIGN PATENT DOCUMENTS

| DE | 3440352 | 11/1984 | |
|---|---|---|---|
| EP | 0470703 | 2/1992 | ............ A61K/9/06 |
| EP | 0590655 | 4/1994 | ............ A61K/9/00 |
| EP | 0 88 770 A | 7/1997 | ............ A61K/9/00 |
| EP | 1048304 | 11/2000 | ............ A61L/27/34 |
| JP | 8143632 | 6/1996 | |
| WO | WO 9406485 | 3/1994 | ............ A61L/27/00 |
| WO | WO 95/04609 | 2/1995 | ............ B05D/7/24 |
| WO | WO 0109646 | 2/2001 | .............. C08J/7/04 |
| WO | WO 0182984 | 11/2001 | ............ A61L/12/14 |

OTHER PUBLICATIONS

Swant, A. D., M. Gabriel, M. S. Mayo, and D. G. Ahearn. 1991. Radioopacity additives in silicone stent materials reduce in vitro bacterial adherence. Curr. Microbiol. 22:285–292.

Gabriel, M. M., A. D. Sawant, R. B. Simmons, and D. G. Ahearn. 1995. Effects of sliver on adherence of bacteria to urinary catheter: in vitro studies. Curr. Microbio. 30:17–22.

"A Relatively Small Change in Sodium Chloride Concentration has a Strong Effect on Adhesion of Ocular Bacteria to Contact Lenses" by B. Cowell, et al., *Journal of Applied Microbiology*, 1998, vol. 84, pp. 950–958.

Primary Examiner—Krisanne Thornton
(74) Attorney, Agent, or Firm—Rita D. Vacca; Robert B. Furr, Jr.

(57) ABSTRACT

A method is disclosed for inhibiting adhesion of bacteria to the surface of a biomedical device comprising contacting the surface of said biomedical device with a cationic polysaccharide in aqueous solution having an ionic strength of from about 0.01 to about 0.13.

23 Claims, No Drawings

U.S. PATENT DOCUMENTS

| | | |
|---|---|---|
| 5,858,937 A | 1/1999 | Richard et al. .............. 510/112 |
| 5,872,086 A | 2/1999 | Ellis et al. ................... 510/112 |
| 5,908,906 A | 6/1999 | Kunzler et al. ............. 526/279 |
| 5,914,355 A | 6/1999 | Kunzler ...................... 523/106 |
| 5,945,153 A | 8/1999 | Dearnaley .................. 427/2.12 |
| 5,945,465 A | 8/1999 | Ozark et al. ................ 523/106 |
| 5,961,958 A | 10/1999 | Homola et al. ............... 424/49 |
| 5,969,076 A | 10/1999 | Lai et al. ...................... 528/28 |
| 5,980,868 A | 11/1999 | Homola et al. ................ 424/54 |
| 5,981,669 A | 11/1999 | Valint, Jr. et al. ........... 525/477 |
| 5,984,905 A | 11/1999 | Dearnaley .................... 604/265 |
| 6,001,823 A | 12/1999 | Hultgren et al. ............... 514/99 |
| 6,008,317 A | 12/1999 | Lai et al. ..................... 528/374 |
| 6,013,106 A | 1/2000 | Tweden et al. ............... 623/66 |
| 6,037,328 A | 3/2000 | Hu et al. ...................... 514/23 |
| 6,054,054 A | 4/2000 | Robertson et al. ......... 210/698 |
| 6,071,439 A | 6/2000 | Bawa et al. ................. 264/1.1 |

LOW IONIC STRENGTH METHOD AND COMPOSITION FOR REDUCING BACTERIAL ATTACHMENT TO BIOMATERIALS

FIELD OF THE INVENTION

The present invention is directed to the surface treatment of medical devices including ophthalmic lenses, stents, implants and catheters. In particular, the present invention is directed to a simple, low cost method of modifying the surface of a medical device to decrease its affinity for bacterial adhesion.

BACKGROUND

Medical devices such as ophthalmic lenses have been investigated for a number of years. Such materials can generally be subdivided into two major classes, namely hydrogels and non-hydrogels. Non-hydrogels do not absorb appreciable amounts of water, whereas hydrogels can absorb and retain water in an equilibrium state.

Those skilled in the art have long recognized that surface characteristics play a major role in biocompatibility. It is known that increasing the hydrophilicity of the contact lens surface improves the wettability of the contact lenses. This in turn is associated with improved wear comfort of contact lenses. Additionally, the surface of the lens can affect the lens's susceptibility to deposition, particularly the deposition of proteins and lipids from the tear fluid during lens wear. Accumulated deposition can cause eye discomfort or even inflammation. In the case of extended wear lenses (i.e. lenses used without daily removal of the lens before sleep), the surface is especially important, since extended wear lenses must be designed for high standards of comfort and biocompatibility over an extended period of time.

Extended-wear lenses also present two added challenges. First, the lenses are typically in continuous contact with the epithelium for between 7 and 30 days. This stands in marked contrast to conventional contact lenses, which are removed from the eye before sleep. Second, because the extended-wear lenses are worn continuously, they are generally not removed for disinfection until the conclusion of the recommended extended-wear period. Thus an improved method for inhibiting bacterial attachment would be a major advance for both conventional and extended-wear contact lenses.

In the area of contact lens wetting/conditioning solutions, it has been found that polyelectrolytes can bind to a lens surface of opposite charge and form polyelectrolyte complexes. Such polyelectrolyte complexes have commercially been demonstrated to give more comfortable lens materials because of the greater adsorption of surface bound water. Examples of materials useful for forming such polyelectrolyte complexes are taught in U.S. Pat. No. 4,321,261 to Ellis et al.; U.S. Pat. No. 4,436,730 to Ellis et al.; U.S. Pat. No. 5,401,327 to Ellis et al.; U.S. Pat. No. 5,405,878 to Ellis et al.; U.S. Pat. No. 5,500,144 to Potini et al.; U.S. Pat. No. 5,604,189 to Zhang et al.; U.S. Pat. No. 5,711,823 to Ellis et al.; U.S. Pat. No. 5,773,396 to Zhang et al.; and U.S. Pat. No. 5,872,086 to Ellis et al.

Bacterial attachment to biomaterial surfaces is believed to be a contributing factor in device-related infection. But the extent to which a given microorganism will attach itself to a given biomaterial has proven difficult to predict. Examples of methods for inhibiting such attachment are taught in U.S. Pat. No. 5,945,153 to Dearnaley; U.S. Pat. No. 5,961,958 to Homola et al.; U.S. Pat. No. 5,980,868 to Homola et al.; U.S. Pat. No. 5,984,905 to Dearnaley; U.S. Pat. No. 6,001,823 to Hultgren et al.; U.S. Pat. No. 6,013,106 to Tweden et al.; and U.S. Pat. No. 6,054,054 to Robertson et al.

For contact lens materials, bacterial attachment to a lens surface can lead to bacterial keratitis, or other potential contact lens related complications such as sterile infiltrates and CLARE (Contact Lens Induced Acute Red Eye). Thus it would be desirable to provide a method for inhibiting attachment of microorganisms to contact lenses.

SUMMARY OF THE INVENTION

This invention provides a method for inhibiting the attachment of microorganisms to the surface of a biomaterial. In accordance with the invention, it has been found that controlling the ionic strength of the solution unexpectedly affects the performance of the cationic cellulosic polymer for inhibiting bacterial attachment. Specifically, it has been found that solutions having an ionic strength of less than about 0.13, preferably less than about 0.10 are notably effective for decreasing bacterial attachment to biomedical materials. The range of useful ionic strengths in accordance with this invention is from about 0.01 to about 0.13, preferably from about 0.05 to about 0.10. In a preferred embodiment, the biomedical material is a contact lens and the cationic polysaccharide is a cationic cellulosic polymer. In a more preferred embodiment, the solution has an ionic strength as defined here of less than about 0.095 and most preferably less than about 0.090. The method of the invention is well suited for use with contact lenses, especially silicone hydrogel contact lenses suitable for continuous wear for about 7 to about 30 days.

In another embodiment, the invention provides a composition for inhibiting the attachment of microorganisms to the surface of a biomaterial. The composition of the invention comprises a cationic polysaccharide in an aqueous solution having an ionic strength as defined herein of less than about 0.13, preferably less than about 0.10, more preferably less than about 0.095 and most preferably less than about 0.090. In a preferred embodiment of the composition, the cationic polysaccharide is a cationic cellulosic polymer.

The surface of the biomaterial is preferably at least slightly anionic prior to the application of the cationic polysaccharide. The mechanism for binding the cationic polysaccharide to the surface of the biomedical device is not critical, provided that the binding strength is sufficient to maintain the surface for the intended use of the biomaterial. As used herein, the terms "bond" and "bind" refer to forming a relatively stable complex or other relatively stable attraction between the surface of a biomedical device and a polysaccharide with or without the addition of a linking agent, and is not limited to a particular mechanism. Thus "binding" may involve covalent bonds, hydrogen bonds, hydrophobic interactions or other molecular interactions that enable the cationic polysaccharide of the invention to form a relatively tenacious surface coating on a biomedical device.

The cationic charge on the cationic polysaccharide may be derived from ammonium groups, quaternary ammonium groups, guanidium groups, sulfonium groups, phosphonium groups, bound transition metals, and other positively charged functional groups.

Examples of methods for providing an anionic surface charge on the biomedical device include: (a) bulk distribution of anionic sites in the biomaterial for example, by polymerization; (b) oxidative surface treatment such as plasma discharge or corona discharge; (c) application of an anionic linking agent; (d) complexation; or (e) a combination of one or more of (a)–(d).

Incorporating monomers containing groups such as carboxylate groups, sulfate groups, sulfonate groups, sulfite groups, phosphate groups, phosphonate groups, and phosphonic groups can provide anionic sites distributed through the bulk of the polymeric substrate material. Methacrylic acid and 2-acrylamido-2-methylpropane sulfonic acid are examples of monomers that are useful for incorporating negatively charged sites into the bulk of the substrate biomaterial.

If the surface of the biomaterial carries a net neutral charge or a net cationic charge, the biomaterial may be treated with an oxidative surface treatment or other surface treatment to present a net anionic charge prior to the treatment with the cationic polysaccharide. Examples of suitable oxidative surface treatments include plasma discharge or corona discharge as taught in U.S. Pat. No. 4,217,038 to Letter; U.S. Pat. No. 4,096,315 to Kubacki; U.S. Pat. No. 4,312,575 to Peyman; U.S. Pat. No. 4,631,435 to Yanighara; and U.S. Pat. Nos. 5,153,072; 5,091,204 and 4,565,083, all to Ratner. Additional examples of plasma surface treatments include subjecting contact lens surfaces to a plasma comprising an inert gas or oxygen (see, for example, U.S. Pat. Nos. 4,055,378; 4,122,942; and 4,214,014); various hydrocarbon monomers (see, for example, U.S. Pat. No. 4,143,949); and combinations of oxidizing agents and hydrocarbons such as water and ethanol (see, for example, WO 95/04609 and U.S. Pat. No 4,632,844). These patents are incorporated by reference as if set forth at length herein.

The cationic polysaccharide may attach to the surface of the biomaterial through interactions between hydrophobic sites on the biomaterial surface interacting with hydrophobic groups on the cationic polysaccharide. Covalent linkages may also exist between the surface of the biomaterial and the water-soluble cationic polysaccharide such that the cationic polysaccharide is bound to the biomaterial surface.

The cationic polysaccharide may also bind to the surface of the biomedical device through hydrogen-bonding interactions. These hydrogen-bonding interactions may occur between hydrogen-bond accepting surfaces and hydrogen-bond donating solutions, or between hydrogen-bond donating surfaces and hydrogen-bond accepting solutions. Examples of hydrogen-bond accepting groups include pyrrolidone groups, acrylamide groups, polyether groups and fluorocarbon groups. Examples of suitable polyether groups include poly(ethylene glycol) or poly(ethylene oxide). Examples of suitable hydrogen-donating groups include carboxylic acids, sulfuric acids, sulfonic acids, sulfinic acids, phosphoric acids, phosphonic acids, phosphinic acids, phenolic groups, hydroxy groups, amino groups and imino groups.

Examples of linkages include those provided by coupling agents such as ester linkages and amide linkages. Surface linkages may also include surface complexations. Examples of such surface complexations include the reaction products formed by treating a biomaterial comprising a hydrophilic monomer and a silicone-containing monomer with a proton-donating wetting agent, where the wetting agent forms a complex with hydrophilic monomer on the surface of the biomaterial in the absence of a surface oxidation treatment step.

The biomedical device may be an ophthalmic lens, for example an intraocular lens, a contact lens or a corneal inlay. The biomedical device may also be a contact lens case, more particularly the interior portion of a contact lens case. The method of the invention is useful with soft lens materials such as hydrogels as well as with rigid contact lens materials. The method of the invention is especially useful with extended-wear contact lenses that are suitable for periods of continuous wear for about 7 to about 30 days.

The cationic cellulosic polymers of the invention have been found to exhibit strong anti-attachment properties (activity) for the bacterium, *Pseudomonus aeruginosa*, as shown in studies of attachment to contact lens surfaces. Examples of useful cationic polysaccharides are derived from the families based on cellulosics, guar gum, starch, dextran, chitosan, locust bean gum, gum tragacanth, curdlan, pullulan and seleroglucan. Of particular interest are the cationic polymers derived from cellulosic materials. It is believed that the degree of inhibition activity is related to the strength of the ionic bonding between the polymeric surface coating and the lens surface. Thus, independent of the mechanism, stronger bonds are believed to be associated with a greater degree of resistance to bacterial adhesion.

The layer or coating comprises a polyelectrolyte complex which is formed by complexation of an ionic lens surface with an oppositely charged ionic polymer, and this complex forms a hydrogel at the lens surface which absorbs water, has good water retention, and is compatible with the physiological structures of the eye. A durable "cushion" is formed which provides long lasting comfort to the eye. For a discussion of the measurement of polymer-surfactant interactions, see Argillier et al. "Polymer-Surfactant Interactions Studied with the Surface Force Apparatus" 146 *Journal of Colloid and Interface Science* 242 (1991).

In accordance with the present invention, it has been found that controlling the ionic strength of the wetting solution surprisingly improves the durability of the polymeric cushion formed on the surface of the contact lens.

The solutions of the invention are characterized herein using the term "ionic strength". The term "ionic strength" as used herein is a dimensionless number defined by the equation:

Ionic strength=$0.5\Sigma(C_i Z_i^2)$, where $C_i$ is the molar concentration of ionic species i, and $Z_i$ is the valence of ionic species i.

The ionic strength of the solution of the present invention is less than about 0.10, preferably less than about 0.095 and more preferably less than about 0.090. For a more detailed discussion of the term "ionic strength", see Remington's Pharmaceutical Sciences, $17^{th}$ ed., published by Philadelphia College of Pharmacy and Science (1985). The contact lens is preferably an oxygen permeable hard lens that carries an ionic charge or has the potential of having an ionic charge.

Preferably the charge of the lens surface is anionic, while that of the polymer in the ophthalmic solution is a cellulosic polymer of cationic charge. The cellulosic polymer should be compatible with the eye, should be non-irritating and yet should form a hydrogel that is electrostatically bound to the surface of the contact lens.

Preferably the lens coating is formed by merely immersing the lens in a solution which consists essentially of an ionic polymer dissolved in a water solution or a water solution containing soluble organic components comprising from 0.001 to 10% by weight of the solution. The ionic polymer can be any ionic polymer compatible with the eye and which does not cause eye irritation yet which forms a hydrogel and which is electrostatically bound to the surface of the contact lens.

DETAILED DESCRIPTION OF THE INVENTION

The invention is applicable to a wide variety of biomaterials, including ophthalmic lens materials as mentioned above. Examples of ophthalmic lenses include contact lenses, anterior and posterior chamber lenses, intraocular lenses and corneal inlays. Ophthalmic lenses may be fabricated from flexible or rigid materials, depending upon the characteristics needed for a particular application.

Substrate Materials

Hydrogels comprise hydrated, crosslinked polymeric systems containing water in an equilibrium state. Conventional hydrogel lens materials include polymers containing monomers such as 2-hydroxyethyl methacrylate (HEMA), glyceryl methacrylate, N-vinylpyrrolidone (NVP) and dimethacrylamide.

Flexible ophthalmic lens materials useful in the present invention include silicone hydrogels as well as conventional hydrogels and low-water elastomeric materials. Examples of flexible ophthalmic lens materials useful in the present invention are taught in U.S. Pat. No. 5,908,906 to Künzler et al.; U.S. Pat. No. 5,714,557 to Künzler et al.; U.S. Pat. No. 5,710,302 to Künzler et al.; U.S. Pat. No. 5,708,094 to Lai et al.; U.S. Pat. No. 5,616,757 to Bambury et al.; U.S. Pat. No. 5,610,252 to Bambury et al.; U.S. Pat. No. 5,512,205 to Lai; U.S. Pat. No. 5,449,729 to Lai; U.S. Pat. No. 5,387,662 to Künzler et al. and U.S. Pat. No. 5,310,779 to Lai; which patents are incorporated by reference as if set forth at length herein.

U.S. Pat. Nos. 6,037,328, 6,008,317, 5,981,675, 5,981,669, 5,969,076, 5,945,465, 5,914,355, 5,858,937, 5,824,719 and 5,726,733 teach ophthalmic lens materials containing HEMA monomers.

U.S. Pat. Nos. 6,071,439, 5,824,719, 5,726,733, 5,708,094, 5,610,204, 5,298,533, 5,270,418, 5,236,969 and 5,006,622 teach ophthalmic lens materials containing glyceryl methacrylate monomers.

U.S. Pat. Nos. 6,008,317, 5,969,076, 5,908,906, 5,824,719, 5,726,733, 5,714,557, 5,710,302, 5,708,094, 5,648,515 and 5,639,908 teach ophthalmic lens materials containing NVP monomers.

U.S. Pat. Nos. 5,539,016, 5,512,205, 5,449,729, 5,387,662, 5,321,108 and 5,310,779, teach ophthalmic lens materials containing dimethacrylamide monomers.

The preferred conventional hydrogel materials typically contain HEMA, NVP and TBE (4-t-butyl-2-hydroxycyclohexyl methacrylate). Polymacon™ materials, for example the Soflens 66™ brand contact lenses (commercially available from Bausch & Lomb Incorporated of Rochester, N.Y.), are examples of particularly preferred conventional hydrogel materials.

Silicone hydrogels generally have a water content greater than about five weight percent and more commonly between about ten to about eighty weight percent. Materials are usually prepared by polymerizing a mixture containing at least one silicone-containing monomer and at least one hydrophilic monomer. Either the silicone-containing monomer or the hydrophilic monomer may function as a crosslinking agent (a crosslinker being defined as a monomer having multiple polymerizable functionalities) or a separate crosslinker may be employed. Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

A preferred silicone hydrogel material comprises (in the bulk monomer mixture that is copolymerized) 5 to 50 percent, preferably 10 to 25, by weight of one or more silicone macromonomers, 5 to 75 percent, preferably 30 to 60 percent, by weight of one or more polysiloxanylalkyl (meth)acrylic monomers, and 10 to 50 percent, preferably 20 to 40 percent, by weight of a hydrophilic monomer. In general, the silicone macromonomer is a poly (organosiloxane) capped with an unsaturated group at two or more ends of the molecule. In addition to the end groups in the above structural formulas, U.S. Pat. No. 4,153,641 to Deichert et al. discloses additional unsaturated groups, including acryloxy or methacryloxy. Fumarate-containing materials such as those taught in U.S. Pat. Nos. 5,512,205; 5,449,729; and 5,310,779 to Lai are also useful substrates in accordance with the invention. Preferably, the silane macromonomer is a silicon-containing vinyl carbonate or vinyl carbamate or a polyurethane-polysiloxane having one or more hard-soft-hard blocks and end-capped with a hydrophilic monomer.

Suitable hydrophilic monomers include those monomers that, once polymerized, can form a complex with poly (acrylic acid). The suitable monomers form hydrogels useful in the present invention and include, for example, monomers that form complexes with poly(acrylic acid) and its derivatives. Examples of useful monomers include amides such as N,N-dimethyl acrylamide, N,N-dimethyl methacrylamide, cyclic lactams such as N-vinyl-2-pyrrolidone and poly (alkene glycol)s functionalized with polymerizable groups. Examples of useful functionalized poly(alkene glycol)s include poly(diethylene glycol)s of varying chain length containing monomethacrylate or dimethacrylate end caps. In a preferred embodiment, the poly(alkene glycol) polymer contains at least two alkene glycol monomeric units. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. In a particularly preferred embodiment, the hydrophilic monomers used in the contact lens material are capable of forming a stable complex with a cationic polysaccharide.

Rigid ophthalmic lens materials include rigid-gas-permeable ("RGP") materials. RGP materials typically comprise a hydrophobic crosslinked polymer system containing less than 5 wt. % water. RGP materials useful in accordance with the present invention include those materials taught in U.S. Pat. No. 4,826,936 to Ellis; U.S. Pat. No. 4,463,149 to Ellis; U.S. Pat. No. 4,604,479 to Ellis; U.S. Pat. No. 4,686,267 to Ellis et al.; U.S. Pat. No. 4,826,936 to Ellis; U.S. Pat. No. 4,996,275 to Ellis et al.; U.S. Pat. No. 5,032,658 to Baron et al.; U.S. Pat. No. 5,070,215 to Bambury et al.; U.S. Pat. No. 5,177,165 to Valint et al.; U.S. Pat. No. 5,177,168 to Baron et al.; U.S. Pat. No. 5,219,965 to Valint et al.; U.S. Pat. No. 5,336,797 to McGee and Valint; U.S. Pat. No. 5,358,995 to Lai et al.; U.S. Pat. No. 5,364,918 to Valint et al.; U.S. Pat. No. 5,610,252 to Bambury et al.; U.S. Pat. No. 5,708,094 to Lai et al; and U.S. Pat. No. 5,981,669 to Valint et al. U.S. Pat. No. 5,346,976 to Ellis et al. teaches a preferred method of making an RGP material. The patents mentioned above are incorporated by reference as if set forth at length herein.

Other non-silicone hydrogels used for extended wear applications are also applicable, provided that surface attachment of the cationic polysaccharide can be achieved. The method of the invention is also useful for treating biomaterials before or after fabrication as a broad range of medical devices including intraocular lenses, artificial corneas, stents and catheters, merely to name a few examples.

Surface Coating Materials

Surface coating materials useful in the present invention include cationic polysaccharides, for example cationic cellulosic polymers. Specific examples include cellulosic polymers containing N,N-dimethylaminoethyl groups (either protonated or quartered) and cellulosic polymers containing N,N-dimethylamino-2-hydroxylpropyl groups (either protonated or quaternized). Cationic cellulosic polymers are commercially available or can be prepared by methods known in the art. As an example, quaternary nitrogen-containing ethoxylated glucosides can be prepared by reacting hydroxyethyl cellulose with a trimethylammonium-substituted epoxide. Various preferred cationic cellulosic polymers are commercially available, for example water-soluble polymers available under the CTFA (Cosmetic, Toiletry, and Fragrance Association) designation Polyquaternium-10. Such polymers are commercially available under the tradename UCARE® Polymer from Amerchol Corp., Edison, N.J., USA. These polymers contain quaternized N,N-dimethylamino groups along the cellulosic polymer chain. The cationic cellulosic component may be employed in the compositions at about 0.01 to about ten (10) weight percent of the composition, preferably at about 0.05 to about five (5) weight percent, with about 0.1 to about one (1) weight percent being especially preferred. Suitable cationic cellulosic materials have the following formula:

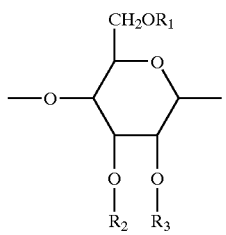

Wherein $R_1$ $R_2$ and $R_3$ are selected from H, derivatives of $C_1$–$C_{20}$ carboxylic acid, $C_1$–$C_{20}$ alkyl groups, $C_1$ to $C_3$ monohydric and dihydric alkanols, hydroxyethyl groups, hydroxypropyl groups, ethylene oxide groups, propylene oxide groups, phenyl groups, "Z" groups and combinations thereof. At least one of $R_1$, $R_2$, and $R_3$ is a Z group.

The nature of the "Z" groups is:

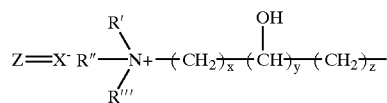

where:

R', R" and R'" can be H, $CH_3$, $C_2H_5$, $CH_2CH_2OH$ and

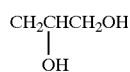

x=0–5, y=0–4, and z=0–5

$X^-$=$Cl^-$, $Br^-$, $I^-$, $HSO_4^-$, $CH_3SO_4^-$, $H_2PO_4^-$, $NO_3^{31}$

U.S. Pat. No. 5,645,827 to Marlin, et al. (incorporated by reference as if set forth at length herein for a discussion of cationic polysaccharides) discloses the use of compositions comprising a cationic polysaccharide in combination with an anionic therapeutic agent, for example, hyaluronic acid or its salt, which is a known demulcent for the treatment of dry eye. European Application 088770 A1 to Marlin et al. discloses cationic cellulose polymers to deliver cationic therapeutic agents, especially for the treatment of glaucoma.

U.S. Pat. Nos. 4,436,730 and 5,401,327 to Ellis, et al. (which are incorporated by reference as if set forth at length herein) disclose the use of cationic cellulosic derivatives in contact-lens treating solutions, including the combination of a cationic cellulose polymer and an ethoxylated glucose such as glucam. In a preferred embodiment, the cationic cellulosic polymer is a Polyquaternium-10 (CAS Numbers 53568-66-4; 55353-19-0; 54351-50-7; 81859-24-7; 68610-92-4; and 81859-24-7). In a more preferred embodiment, the Polyquaternium-10 is Polymer JR-30M, commercially available from Union Carbide Corporation, a subsidiary of the Dow Chemical Company of Midland, Mich. Polymer JR-30M is also dislcosed in U.S. Pat. No. 5,872,086 to Ellis et al., which is incorporated by reference as if set forth at length herein.

Optionally, one or more additional polymeric or non-polymeric demulcents may be combined with the above-named ingredients. Demulcents are known to provide wetting, moisturizing and/or lubricating effects, resulting in increased comfort. Polymeric demulcents can also act as a water-soluble viscosity builder. Included among the water-soluble viscosity builders are the non-ionic cellulosic polymers like methyl cellulose, hydroxyethyl cellulose, hydroxypropyl cellulose, hydroxypropyl methylcellulose and carboxymethyl cellulose, poly(N-vinylpyrrolidone), poly (vinyl alcohol) and the like. Such viscosity builders or demulcents may be employed in a total amount ranging from about 0.01 to about 5.0 weight percent or less. The viscosity of the final formulation ranges from 2 centipoise (cps) to several million cps depending upon whether the formulation is intended for contact lenses, intraocular lenses or corneal inlays. Comfort agents such as glycerin or propylene glycol can also be added.

The present composition may also contain a disinfecting amount of a preservative or an antimicrobial agent. The presence of an antimicrobial agent is not required; however, for the invention to reduce effectively the concentration of bacteria on the surface of a biomaterial, a particularly preferred preservative is sorbic acid (0.15%). Antimicrobial agents are defined as organic chemicals that derive their antimicrobial activity through a chemical or physiochemical interaction with the microbial organisms. For example, biguanides include the free bases or salts of alexidine, chlorhexidine, hexamethylene biguanides and their polymers, and combinations of the foregoing. The salts of alexidine and chlorhexidine can be either organic or inorganic and are typically gluconates, nitrates, acetates, phosphates, sulfates, halides and the like. The preferred biguanide is the hexamethylene biguanide commercially available from Zeneca, Wilmington, Del. under the trademark Cosmocil™ CQ. Generally, the hexamethylene biguanide polymers, also referred to as polyaminopropyl biguanide (PAPB), have molecular weights of up to about 100,000.

If used in the subject solution, the antimicrobial agent should be used in an amount that will at least partially reduce the microorganism population in the formulations employed. Preferably, a disinfecting amount is that which will reduce the microbial bioburden by two log orders in four hours and more preferably by one log order in one hour. Most preferably, a disinfecting amount is an amount which will eliminate the microbial burden on a contact lens when used in regimen for the recommended soaking time (FDA Chemical Disinfection Efficacy Test-July, 1985 Contact Lens Solution Draft Guidelines). Typically, such agents are present in concentrations ranging from about 0.00001 to about 0.5% (w/v), and more preferably, from about 0.00003 to about 0.05% (w/v).

The aqueous solutions employed in this invention may contain, in addition to the active ingredients described above, one or more other components that are commonly present in ophthalmic solutions, for example, buffers, stabilizers, tonicity agents and the like, which aid in making ophthalmic compositions more comfortable to the user. The aqueous solutions of the present invention are typically adjusted with tonicity agents to approximate the tonicity of normal lacrimal fluids which is equivalent to a 0.9% solution of sodium chloride or 2.8% of glycerol solution. The solutions are made substantially isotonic with physiological saline used alone or in combination; otherwise, if simply blended with sterile water and made hypotonic or made hypertonic, the lenses will lose their desirable optical parameters. Correspondingly, excess salt or other tonicity agents may result in the formation of a hypertonic solution that will cause stinging and eye irritation.

The pH of the present solutions should be maintained within the range of 5.0 to 8.0, more preferably about 6.0 to 8.0, most preferably about 6.5 to 7.8; suitable buffers may be added, such as borate, citrate, bicarbonate, TRIS and various mixed phosphate buffers (including combinations of $Na_2HPO_4$, $NaH_2PO_4$ and $KH_2PO_4$) and mixtures thereof. Borate buffers are preferred, particularly for enhancing the efficacy of PAPB. Generally, buffers will be used in amounts ranging from about 0.05 to 2.5 percent by weight, and preferably, from 0.1 to 1.5 percent.

In addition to buffering agents, in some instances it may be desirable to include sequestering agents in the present solutions in order to bind metal ions, which might otherwise react with the lens and/or protein deposits and collect on the lens. Ethylenediaminetetraacetic acid (EDTA) and its salts (disodium) are preferred examples. They are usually added in amounts ranging from about 0.01 to about 0.2 weight percent.

The solutions employed in the present invention can be prepared by a variety of techniques. One method employs two-phase compounding procedures. In the first phase, about 30 percent of the distilled water is used to dissolve the cationic cellulosic polymer by mixing for about 30 minutes at around 50° C. The first-phase solution is then autoclaved at about 120° C. for 30 minutes. In a second phase, alkali metal chlorides, sequestering agents, preservatives and buffering agents are then dissolved in about 60 percent of the distilled water under agitation, followed by the balance of distilled water. The second-phase solution can then be sterilely added into the first-phase solution by forcing it through an 0.22 micron filter by means of pressure, followed by packaging in sterilized plastic containers.

As indicated above, the present invention is useful for improving comfort and wearability for extended-wear contact lenses. For that purpose, compositions for use in the present invention may be formulated as eye-drops and sold in a wide range of small-volume containers from 1 to 30 ml in size. Such containers can be made from HDPE (high density polyethylene), LDPE (low density polyethylene), polypropylene, poly(ethylene terepthalate) and the like. Flexible bottles having conventional eye-drop dispensing tops are especially suitable for use with the present invention. The eye-drop formulation of the invention used by instilling, for example, about one (1) or three (3) drops in the eye(s) as needed.

The present invention is also useful as a component of a cleaning, disinfecting or conditioning solution. The invention may also include antimicrobial agents, surfactants, toxicity adjusting agents, buffers and the like that are known to be useful components of conditioning and/or cleaning solutions for contact lenses. Examples of suitable formulations for cleaning and/or disinfecting solutions are taught in U.S. Pat. No. 5,858,937 to Richard and Heiler, which is incorporated by reference as if set forth at length herein.

EXAMPLES

The Examples use the following terms and tradenames.
1. Polymer JR 30M™ is a preferred polymeric quaternary ammonium salt of hydroxyethyl cellulose reacted with a trimethyl ammonium substituted expoxide, and is a cationic cellulosic polymer of the class of known as Polyquaterium-10. Polymer JR 30M™ is commercially available from Union Carbide Corporation, a subsidiary of the Dow Chemical Company of Midland, Mich.
2. HEC is hydroxyethylcellulose.
3. Pluronic F127™ (also referred to as "F127") is a nonionic surfactant that is a block copolymer of propylene oxide and ethylene oxide. The propylene oxide block is sandwiched between two ethylene oxide blocks. This nonionic surfactant is commercially available from BASF Corporation, Specialty Products Business Group, 3000 Continental Drive North, Mount Olive, N.J. 07828-1234.
4. Kollidon 30™ is a tradename for povidone of medium molecular weight (Mw 44,000–54,000). Kollidon 30 is commercially available from BASF Corporation, 3000 Continental Drive North, Mount Olive, N.J. 07828-1234.
5. PVA Airvol 603™ is poly(vinyl alcohol) (PVOH), commercially available from Air Products and Chemicals, Inc., 7201 Hamilton Boulevard, Allentown, Pa. 18195-1501.

Example 1

Surface Conditioning of Surevue Lenses with Polymer JR

This example illustrates the binding effect of the cationic cellulosic polymer onto hydrophilic contact lenses, where it is believed to reduce the attachment of bacteria to the material surface. Three Surevue lenses (manufactured by Johnson & Johnson, New Brunswick, N.J.) in three different solutions were submitted for comparison by Atomic Force Microscopy (AFM) analysis. Solution 1, for comparison, was a Blank Borate-Buffered Saline. Solution 2 was Solution 1 with 0.1% Polymer JR. Solution 3, for further comparison, was ReNu® MPS (manufactured by Bausch & Lomb, Rochester, N.Y.). The lenses were treated overnight, and then removed from the vials and desalinated in HPLC grade water in a static fashion for a minimum of 15 minutes. All lenses were cut with a clean scalpel on a clean glass substrate. The samples were dried, sectioned and placed on a clean substrate. Three 50×50 $\mu$m topographical images were acquired for each side (anterior and posterior) of the lenses using AFM. The AFM used in this study was the Dimension 3000 and was operated in ContactMode. The AFM works by measuring nano-scale forces ($10^{-9}$N) between a sharp probe and atoms on the lens surface. The resulting AFM images showed that the anterior and posterior surfaces of the lenses stored in Blank Borate-Buffered Saline (Solution 1) as well as ReNu® MPS (Solution 3) showed no significant topographical change. The anterior and posterior surfaces of the lenses stored in Polymer JR solution (Solution 2) showed a significantly different topography. The surface is covered with a thin film, with multi-sized and shaped voids covering both anterior and posterior surfaces. These voids had an average depth of 40±10 nm. These void-like anomalies were not present in the lenses stored in Solution 2 or Solution 3. The voids had an effect on the Root Mean Square (RMS) roughness for the lenses stored in the Polymer JR solution.

The RMS surface roughness (shown in Table below) was calculated using the Nanoscope software The lenses stored in Solution 1 or Solution 3 had a smoother anterior and posterior surface compared to the anterior and posterior of lenses stored in the Polymer JR solution.

TABLE 1

RMS Roughness for Each Set of AFM Images

| Solution | Anterior | Posterior | Mean |
|---|---|---|---|
| Solution 1 | 3.93 nm | 3.03 nm | 3.48 nm |
| Solution 2 | 8.85 nm | 6.21 nm | 7.53 nm |
| Solution 3 | 5.82 nm | 3.09 nm | 4.46 nm |

The AFM results indicate that Polymer JR has an effect on the morphology of the lens surface, indicating a thin film covering with large multi-shaped and sized voids on the anterior and posterior side of the lens.

Example 2

Aliquots of 20 ml of 0.1% cationic Polymer JR solution were poured into sterile polystyrene disposable petri dishes. Negatively charged continuous wear lenses were removed from the packages with a sterile forceps and immersed five times in 180 ml of initially sterile 0.9% saline. These lenses were then placed into petri dishes containing 0.1 % Polymer JR solutions and soaked for 4 h at room temperature. After 4 h incubation time, the ionically coated lenses were removed from the 0.1% Polymer JR solution with a sterile forceps and immersed 5 times in each of three successive changes (180ml) of initially sterile 0.9% saline. The lenses were then transferred to 20-ml glass scintillation vials containing 3 ml of ~$10^8$ cells/ml inoculum of radiolabeled cells and were incubated at 37° C. for 2 h.

Examples 3 and 4

Examples 3 and 4 evaluate bacterial adherence to biomaterials using a radiolabel method.

Adherence studies were conducted with a modification of the procedures of Sawant et al. Radioopacity additives in silicone stent materials reduce in vitro bacterial adherence. (Sawant, A. D., M. Gabriel, M. S. Mayo, and D. G. Ahearn. 1991 Curr. Micorbiol. 22:285–292, and Gabriel, M. M., A. D. Sawant, R. B. Simmons, and D. G. Ahearn. 1995. Effects of sliver on adherence of bacteria to urinary catheter: in vitro studies. Curr. Microbio. 30:17–22.).

Bacterial cells were grown in Triptic Soy Broth (TSB) at 37° C. on a rotary shaker for 12 to 18 h. Cells were harvested by centrifugation at 3000×g for 10 min, washed two times in 0.9% saline and suspended in minimal medium(1.0 g D-glucose, 7.0 g $K_2HPO_4$, 2.0 g $KH_2PO_4$, 0.5 g sodium citrate, 1.0 g $(NH_4)_2SO_4$, and 0.1 g $MgSO_4$ in 1 liter distilled $H_2O$, pH 7.2) to a concentration of about ~$2 \times 10^8$ cells per ml (Optical density 0.10 at 600 nm). The minimal broth cultures were incubated for 1 h at 37° C. with shaking. One to 3 µCi/ml of L-[3,4,5-$^3$H] leucine (NEN Research Products, Du Pont Company, Wilmington, Del.) were added to the cells and the cell suspensions were incubated for another 20 min. These cells were washed 4 times in 0.9% saline and suspended in phosphate buffered saline (PBS) to a concentration of about ~$10^8$ cells per ml (Optical density 0.10 at 600 nm).

Extended-wear contact lenses having a normally anionic surface charge were incubated with 3 ml of the radiolabeled cell suspension at 37° C. for 2 h. These lenses were removed from the cell suspension with a sterile forceps and immersed 5 times in each of three successive changes (180 ml) of initially sterile 0.9% saline. The lenses were shaken free from saline and transferred to 20-ml glass scintillation vials. Ten ml Opti-Fluor scintillation cocktail (Packard Instrument Co., Downers Grove, Ill.) were added to each vial. The vials were vortexed and then placed in a liquid scintillation counter (LS-7500, Beckman Instruments, Inc., Fullerton, Calif.). Data for two experiments were converted from disintegrations per min (dpm) to colony-forming units (cfu) based on a standard calibration curve and expressed as cfu/mm$^2$. Calibration curves were constructed from numbers of colonies recovered in pour plates of serial dilutions of inocula and from optical densities (O.D.s) of serial dilutions of cell suspensions of known densities. Uninoculated extended-wear contact lenses having normally anionic surface charge, which served as controls for the nonspecific uptake of leucine, were treated in the same manner as the inoculated sections.

Examples 5 and 6

Table 2 shows the results of Example 5 and 6, comparing the degree of primary attachment of bacterium *Pseudomonas aeruginosa* on the surface of an extended-wear hydrogel contact lens with and without a surface coating of a cationic cellulosic polymer applied in a two-minute soaking step.

TABLE 2

Two-minute soak with continuous-wear silicone hydrogel lenses

| Example No. | Formulation | CFU/mm$^2$ |
|---|---|---|
| 5 | 0.8% Sodium Chloride<br>0.02% Potassium Chloride<br>0.024% Potassium Phophate Monobasic<br>0.144% Sodium Phosphate Dibasic | $6.56 \times 10^4 \pm 8.53 \times 10^3$ |
| 6 | 0.8% Sodium Chloride<br>0.2% Potassium Chloride<br>0.05% Disodium Edetate<br>0.28% Sodium Phosphate Dibasic<br>0.055% Potassium Phosphate Monobasic<br>0.1% Polymer JR 30M<br>0.625% HEC<br>0.07% Pluronic F127 Surfactant<br>0.3% PVA Airvol 603<br>0.033% Chlorhexidine 20% | $2.44 \times 10^5 \pm 3.51 \times 10^4$ |

Examples 7 and 8

Table 3 shows the results of Examples 7 and 8, comparing the degree of primary attachment of bacterium *Pseudomonas aeruginosa* on the surface of an extended-wear hydrogel contact lens with and without a surface coating of a cationic cellulosic polymer applied in a four-hour soaking step.

TABLE 3

Four-hour soak with continuous-wear silicone hydrogel contact lenses.

| Example No. | Formulation | CFU/mm$^2$ |
|---|---|---|
| 7 | 0.8% Sodium Chloride<br>0.02% Potassium Chloride<br>0.024% Potassium Phophate Monobasic<br>0.144% Sodium Phosphate Dibasic | $7.96 \times 10^4 \pm 1.20 \times 10^4$ |

TABLE 3-continued

Four-hour soak with continuous-wear silicone hydrogel contact lenses.

| Example No. | Formulation | CFU/mm² |
|---|---|---|
| 8 | 0.8% Sodium Chloride<br>0.2% Potassium Chloride<br>0.05% Disodium Edetate<br>0.28% Sodium Phosphate Dibasic<br>0.055% Potassium Phosphate Monobasic<br>0.1% Polymer JR 30M<br>0.625% HEC<br>0.07% F127<br>0.3% PVA Airvol 603<br>0.033% Chlorhexidine 20% | $8.77 \times 10^3 \pm 2.40 \times 10^3$ |

Examples 9–11

Table 4 shows the results of Examples 9–11, comparing the degree of primary attachment of bacterium *Pseudomonas aeruginosa* on the surface of a Group IV contact lens (commercially available from Johnson & Johnson under the tradename Survue™) with the surface coating of a cationic cellulosic polymer versus PVP polymer applied in a four-hour soaking step.

TABLE 4

Four-hour soak with Group IV lenses

| Example No. | Formulation | CFU/mm² |
|---|---|---|
| 9 | 0.8% Sodium Chloride<br>0.02% Potassium Chloride<br>0.024% Potassium Phophate Monobasic<br>0.144% Sodium Phosphate Dibasic | $2.52 \times 10^5 \pm 3.42 \times 10^4$ |
| 10 | 2% PVP Kollidon 30<br>0.66% Boric Acid<br>0.1% Sodium Borate<br>0.53% Sodium Chloride | $2.44 \times 10^5 \pm 3.51 \times 10^4$ |
| 11 | 0.1% Polymer JR 30M<br>0.66% Boric Acid<br>0.1% Sodium Borate<br>0.53% Sodium Chloride | $9.83 \times 10^4 \pm 3.88 \times 10^4$ |

Table 5 shows the results of Example 12–14, comparing the degree of primary attachment of bacterium *Pseudomonas aeruginosa* on the surface of a Group IV contact lens coated with a cationic cellulosic polymer under the environment of the high ionic strength versus the low ionic strength applied in a four-hour soaking step.

TABLE 5

Four-hour soak with Survue ™ lenses.

| Example No. | Formulation | CFU/mm² |
|---|---|---|
| 12 | 0.8% Sodium Chloride<br>0.02% Potassium Chloride<br>0.024% Potassium Phophate Monobasic<br>0.144% Sodium Phosphate Dibasic | $2.52 \times 10^5 \pm 3.42 \times 10^4$ |
| 13 | 0.1% Polymer JR 30M<br>1% PVP Kollidon 30<br>0.66% Boric Acid<br>0.1% Sodium Borate<br>0.53% Sodium Chloride | $2.23 \times 10^5 \pm 6.50 \times 10^4$ |
| 14 | 0.1% Polymer JR 30M<br>1% PVP Kollidon 30<br>0.66% Boric Acid<br>0.1% Sodium Borate<br>1% Glycerin<br>0.5% Propylene Glycol | $3.32 \times 10^4 \pm 7.82 \times 10^3$ |

Many other modifications and variations of the present invention are possible in teachings herein. It is therefore understood that, within the scope of the present invention can be practiced other than as herein specifically described.

What is claimed is:

1. A method for inhibiting adhesion of bacteria to the surface of a biomedical device comprising contacting the surface of said biomedical device with a cationic polysaccharide in aqueous solution having an ionic strength of from about 0.01 to about 0.13.

2. The method of claim 1 wherein said aqueous solution has an ionic strength of from about 0.05 to about 0.1.

3. The method of claim 1 wherein said aqueous solution has an ionic strength of less than about 0.095.

4. The method of claim 3 wherein said aqueous solution has an ionic strength of less than about 0.090.

5. The method of claim 1 further comprising treating the surface of said biomedical device to provide a net anionic charge on said surface before contacting said surface with said cationic polysaccharide.

6. The method of claim 1 wherein the surface of said biomedical device carries a net anionic surface charge and wherein the method includes no intermediate treatment step to modify the surface charge before binding said polysaccharide to the surface of said biomedical device.

7. The method of claim 5 wherein said surface treating step further comprises contacting said surface with a linking agent.

8. The method of claim 1 wherein said contacting step further comprises retaining said cationic polysaccharide on the surface of said biomedical device through at least one selected from the group consisting of ionic interactions, hydrogen-bonded interactions, hydrophobic interactions and covalent interactions.

9. The method of claim 8 wherein said ionic interactions are between oppositely charged ionic groups between the biomedical device and an aqueous solutions containing the cationic polysaccharide.

10. The method of claim 9 wherein the negative charge on the biomedical device is derived from at least one selected from the group consisting of carboxylate groups, sulfonate groups, phosphate groups and phosphonate groups.

11. The method of claim 9 wherein the cationic charge on the cationic polysaccharide is derived from quaternary ammonium groups, sulfonium groups, phosphonium groups, and other positively charged functional groups.

12. The method of claim 8 wherein said hydrogen-bonding interactions occur between hydrogen-bond accepting surfaces and hydrogen-bond donating solutions, or through hydrogen-bond donating surfaces and hydrogen-bond accepting surfaces.

13. The method of claim 12 wherein said hydrogen-bond accepting groups are selected from the group consisting of pyrrolidone groups, N,N-disubstituted acrylamide groups and polyether groups.

14. The method of claim 13 wherein said polyether groups are poly(ethylene glycol) or poly(ethylene oxide).

15. The method of claim 12 wherein said hydrogen-donating groups are selected from the group consisting of carboxylic acids, phosphoric acids, phosphonic acids and phenolic groups.

16. The method of claim 8 wherein said hydrophobic interactions occur through hydrophobic sites on the biomaterial surface interacting with hydrophobic groups on the cationic polysaccharide.

17. The method of claim 7 wherein said covalent interactions exist between the biomaterials surface and the water-soluble cationic polysaccharide such that the cationic polysaccharide is bound to the biomaterial surface.

18. The method of claim 1 wherein said biomedical device is an ophthalmic lens.

19. The method of claim 15 wherein said ophthalmic lens is selected from the group consisting of contact lenses, anterior chamber lenses, posterior chamber lenses intraocular lenses and corneal inlays.

20. The method of claim 1 wherein said biomedical device is a silicone hydrogel material.

21. The method of claim 19 wherein said contact lens is an extended-wear contact lens suitable for periods of continuous wear for about 7 to about 30 days.

22. The method of claim 1 wherein the cationic polysaccharide is selected from the group consisting of cationic starch, cationic dextran, cationic chitosan, cationic locust bean gum, cationic gum tragacanth, cationic curdlan, cationic pullulan and cationic scleroglucan.

23. The method of claim 1 wherein the biomedical device is selected from the group consisting of intraocular lenses, corneal inlays, contact lenses, contact lens cases, stents, implants and cathaters.

* * * * *